US011657914B2

(12) United States Patent
Donnelly et al.

(10) Patent No.: US 11,657,914 B2
(45) Date of Patent: *May 23, 2023

(54) SYSTEMS, METHODS AND DEVICES FOR DYNAMIC PROCEDURE MANAGEMENT

(71) Applicant: ORtelligence, Inc., West Chester, PA (US)

(72) Inventors: Timothy Donnelly, Glen Mills, PA (US); James Krieg, Glen Mills, PA (US); Derek Donegan, Glen Mills, PA (US)

(73) Assignee: ORtelligence, Inc.

( * ) Notice: Subject to any disclaimer, the term of this patent is extended or adjusted under 35 U.S.C. 154(b) by 57 days.

This patent is subject to a terminal disclaimer.

(21) Appl. No.: 17/335,310

(22) Filed: Jun. 1, 2021

(65) Prior Publication Data
US 2021/0287788 A1 Sep. 16, 2021

Related U.S. Application Data

(63) Continuation of application No. 17/186,500, filed on Feb. 26, 2021, now Pat. No. 11,049,611, which is a
(Continued)

(51) Int. Cl.
*G16H 40/40* (2018.01)
*G16H 50/20* (2018.01)
(Continued)

(52) U.S. Cl.
CPC .......... *G16H 40/40* (2018.01); *A61B 5/0022* (2013.01); *A61B 5/6802* (2013.01); *G06F 9/542* (2013.01); *G16H 50/20* (2018.01); *G16H 80/00* (2018.01)

(58) Field of Classification Search
CPC ........ G16H 40/40; G16H 50/20; G16H 40/67; G16H 40/20; G16H 80/00; G06F 9/542; A61B 5/0022; A61B 5/6802
(Continued)

(56) References Cited

U.S. PATENT DOCUMENTS

| 6,970,097 B2 * | 11/2005 | Welles, II | G01S 1/725 340/8.1 |
| 9,827,048 B2 | 11/2017 | Sweeney | |

(Continued)

FOREIGN PATENT DOCUMENTS

| WO | 2005045461 A1 | 5/2005 | |
| WO | WO-2005045461 A1 * | 5/2005 | ............. A61B 5/411 |

OTHER PUBLICATIONS

Islam et al., "The Internet of Things for Health Care: A Comprehensive Survey," Jun. 1, 2015, IEEE Access, vol. 3, pp. 678-708, doi: 10.1109/ACCESS.2015.2437951. (Year: 2015).*
(Continued)

*Primary Examiner* — Joy Chng
(74) *Attorney, Agent, or Firm* — Stradley Ronon Stevens & Young; Philip Foret; David Fitzgibbon

(57) ABSTRACT

A system and process for dynamically managing a procedure. The system includes a data collection device(s) that objectively monitor a subject and transmit such information to the system and real time position components that report on the availability of an individual(s) to perform the procedure. The system reviews the information, provides a subject diagnosis and recommends equipment. The system can also schedule and monitor the procedure. The individual(s) performing the procedure have the option of consulting with relevant experts and visually interacting with the experts.

17 Claims, 5 Drawing Sheets

Related U.S. Application Data continuation of application No. 16/440,259, filed on Jun. 13, 2019, now Pat. No. 11,189,377.

(60) Provisional application No. 62/684,546, filed on Jun. 13, 2018.

(51) Int. Cl.
*G06F 9/54* (2006.01)
*A61B 5/00* (2006.01)
*G16H 80/00* (2018.01)

(58) Field of Classification Search
USPC .......................................................... 705/2–3
See application file for complete search history.

(56) References Cited

U.S. PATENT DOCUMENTS

| | | | |
|---|---|---|---|
| 10,117,722 B2 | 11/2018 | Sweeney | |
| 2005/0102167 A1* | 5/2005 | Kapoor | G16H 40/20 705/3 |
| 2005/0258937 A1* | 11/2005 | Neuwirth | H04B 1/04 340/539.13 |
| 2006/0192655 A1* | 8/2006 | Levin | G06K 7/0008 340/8.1 |
| 2007/0139191 A1* | 6/2007 | Quatro | G06Q 10/08 340/539.2 |
| 2007/0288263 A1* | 12/2007 | Rodgers | G08B 21/22 705/2 |
| 2015/0213225 A1* | 7/2015 | Amarasingham | G16H 50/30 705/2 |
| 2016/0220323 A1 | 8/2016 | Forrest | |

OTHER PUBLICATIONS

Najera, et al., Real-time location and inpatient care systems based on passive RFID, May 2011, Journal of Network and Computer Applications, vol. 34, Issue 3, pp. 980-989, https://doi.org/10.1016/j.jnca.2010.04.011 (Year: 2011).*

Fisher et al., Evaluation of real-time location systems in their hospital contexts, Oct. 2012, International Journal of Medical Informatics, vol. 81, Issue 10, 2012, pp. 705-712, ISSN 1386-5056, https://doi.org/10.1016/j.ijmedinf.2012.07.001 (Year: 2012).*

\* cited by examiner

SYSTEMS, METHODS AND DEVICES FOR DYNAMIC PROCEDURE MANAGEMENT

CROSS-REFERENCE TO RELATED APPLICATION

This application claims the benefit of U.S. patent application Ser. No. 17/186,500 titled, "Systems, Methods and Devices for Dynamic Reconstructive Procedure Management," filed Feb. 26, 2021, which itself claims priority of U.S. patent application Ser. No. 16/440,259 titled "Systems, Methods and Devices for Dynamic Reconstructive Procedure Management," filed Jun. 13, 2019, which itself claims priority of U.S. Provisional Application No. 62/684,546, titled, "Systems, Methods and Devices for Dynamic Reconstructive Procedure Management," filed Jun. 13, 2018, the content of which are incorporated herein by reference in their entirety.

FIELD OF THE INVENTION

The present disclosure relates to systems, methods and devices to: diagnose a subject, determine procedures that can treat the diagnosed condition, identify individuals or team(s) that are available to perform the procedures, identify the equipment the individual(s) or team(s) desired to perform the procedure, and optionally coordinate the delivery of the equipment to the site at which the procedure will be performed with the individual and/or team that will perform the procedure.

BACKGROUND

Conventionally, elements of procedures are manually controlled resulting in expensive and inefficient management of procedures, such as implant surgeries, and potentially degraded quality of care for the patient. For example, a patient may go to a healthcare facility complaining of hip pain. The doctors at the facility may order hip and pelvis x-rays. A second doctor may have to familiarize themselves with the patient's case before reading the x-rays and then making a diagnosis requiring surgical intervention. A surgeon will likely have to familiarize himself with the patient's case, confirm the diagnosis, and then recommend a specific procedure. The surgeon may also have to consult with an implant specialist, who will have to familiarize himself/herself with the patient's case before recommending a specific implant. A surgical team must then be assembled with each member having to familiarize himself/herself with the patient's case. Mistakes can be made, and time delays can occur at any juncture of the process, and time and money can be wasted working throughout the various channels of communication. Minimizing human errors, inefficiencies, and time loss is desirable. The disclosed dynamic procedure management system improves quality of care, reduces chance for such human errors, and improves efficiencies in the process.

SUMMARY

Illustrative and alternative embodiments of a computer-based dynamic procedure management platform that evaluates a subject condition, identifies available individual(s) and/or team(s) to treat the condition, coordinates the delivery of all the equipment the individual(s) and/or team(s) may require to perform the procedure, and optionally schedules the procedure, are described in detail with reference being made to the figures of this application.

In an exemplary, non-limiting embodiment, the system of the invention comprises a software application. The application operates on a mobile computer device or on a computer device. The device is in communication with at least one image recognition device for monitoring the subject and at least one real-time positioning system component linked to an individual who has previously performed the procedure. The application is configured to receive subject information from the data collection device and real-time location information from the individual, and to communicate the subject information and location information through a wired and/or wireless communication network to a server located at a site where the procedure is to be performed or at a location remote from the site.

The system also includes a processor that is in communication through the wired and/or wireless communication network with the software application, as well as the server. The processer is configured to call up from a database of the system, upon communication of the subject information and location information to the server: (1) a plurality of predetermined potential issue manifestations, (2) a plurality of predetermined potential diagnoses, based on the potential issue manifestations, (3) a plurality of predetermined potential procedures for treating the potential diagnoses, and (4) a plurality of available equipment for performing the procedures. All the above data has previously been uploaded to the database by a professional with knowledge of the issue manifestations, diagnoses, procedures, or equipment or an employee, contractor, or agent of the professional.

The processor is further configured to: (1) actively monitor the location information, (2) determine the availability of the individual based on the location information, (3) notify the software application of the availability of the individual, (4) actively monitor the subject information, (5) determine a subject diagnosis by comparing the subject information to the issue manifestations, (6) determine a subject procedure by comparing the individual to the potential procedures for treating the subject diagnosis, (7) determine a needed item by comparing the potential equipment to the subject procedure, and (8) notify the software application of the needed item.

In a non-limiting embodiment, the processor further notifies the software application of the site at which the procedure will be performed.

In another embodiment, a second real-time positioning component may be included with the equipment to perform the procedure, which may permit the processor to further actively monitor the real-time location of the equipment. The processor may also be further configured to determine an estimated travel time of the individual and/or the equipment to the site of the procedure based on real-time positional data related to movement of the individual and/or equipment. The processor may be further configured to coordinate the delivery of the equipment to the site of the procedure with the arrival of the individuals at the site.

In a further embodiment, the software application may be configured to permit a professional, who is at a location remote from the site, to interact with the individual and/or team at the site. In such an embodiment, the remote professional may interact with the individual and/or team via the use of a laser pointer located at the site.

These and other features, aspects and advantages of the present invention will become better understood with reference to the following description and appended claims.

BRIEF DESCRIPTION OF THE FIGURES

Additional aspects, features, and advantages of the invention, as to its system, structure components, configuration, and operability will be understood and become clear when the invention is considered considering the following description of the figures made in conjunction with the accompanying drawings, wherein.

DETAILED DESCRIPTION

Figure 1:
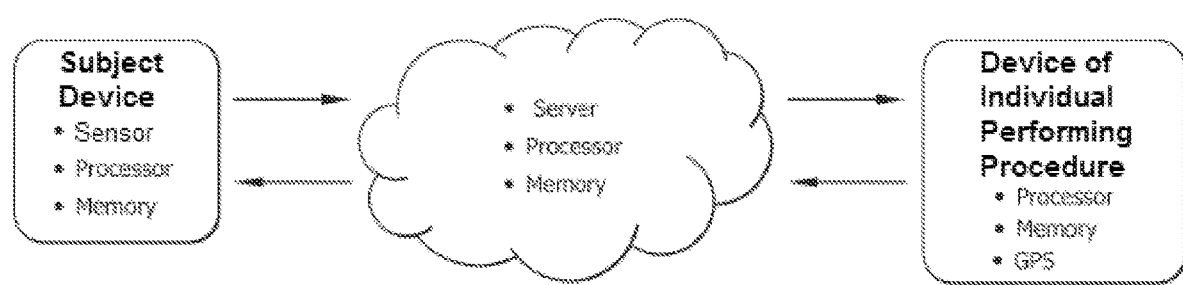
FIG. 1 shows the flow of information between components of the system of the invention.
Figure 2:
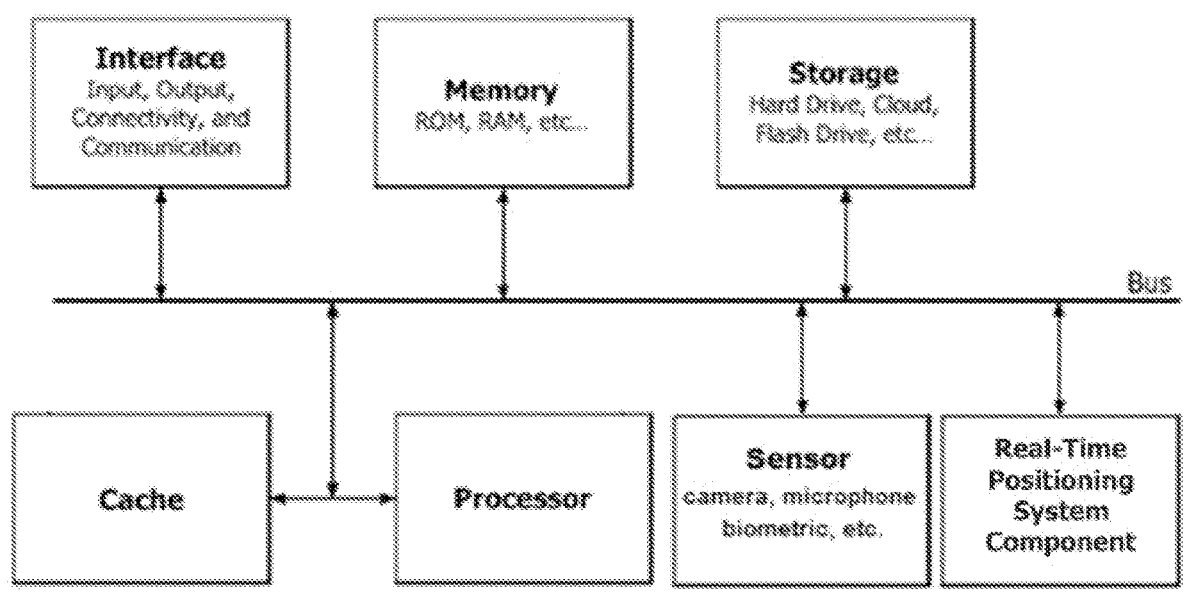
FIG. 2 shows the hardware components of the system of the invention.

Various embodiments of the invention are described in detail below. Although specific implementations are described, this is done for illustration purposes only. A person skilled in the relevant art will recognize that other components and configurations may be used without parting from the spirit and scope of this disclosure.

The invention provides a solution for the present need in the art for systems, methods, and devices for enhancing procedure efficiency. The invention solves the prior art problems using a computer-based platform that is specially programmed to sync data collection device(s) with a software application. The data collection device(s) provide the information to the software application so that an issue may be diagnosed dynamically. From this diagnosis, available procedures to correct the issue may be identified. In addition, the system may monitor available individual(s) and/or team(s) who may perform the procedure via real-time positioning components. Furthermore, the system may also access a list of available equipment and identify specific item(s) the individual(s) and/or team(s) require to perform the procedure.

In one embodiment, the system automatically schedules the procedure with the subject, the individual(s) and/or team(s), and a site where the procedure is to be performed. In such an embodiment, the system automatically coordinates the arrival of the subject and the individual(s) and/or team(s), with the delivery to the site of the items needed to perform the procedure.

In another non-limiting embodiment, the system may be configured to evaluate the individual(s) and/or team(s) prior experiences with each procedure to match the most qualified individual(s) and/or team(s) with the recommended procedure. Furthermore, the system may personalize the procedure and/or equipment based on the individual(s) and/or team(s) performing the procedure. Indeed, the individual(s), or their employee, contractor, or agent may upload an individual profile to the database from which the procedure and/or needed equipment may be personalized. For example, a surgeon who is right-handed may employ a different surgical procedure requiring different surgical equipment than a surgeon who is left-handed. Similarly, a surgeon may be more familiar with one type of implant over another. Such customization may improve the likelihood of the procedure being successful.

In an additional embodiment, the system permits remote professional(s) (e.g., experts) to virtually enter the theater in which the procedure is being performed and physically interact with the individual(s) and/or team(s) via the software application. In such an embodiment, equipment such as a laser pointer may be in the theater. Such equipment may be linked via wired or wireless communication with the remote expert. Such linking may permit the remote expert to control the equipment from their remote location. The remote expert may then talk/direct the individual(s) and/or team(s) through any issues by using the equipment (e.g., laser pointer) to specifically identify the exact element of the subject the remote expert is referencing.

In another embodiment, the need items may be placed on a cart and the remote expert may be granted authorization to control the opening/closing of drawers on the cart. As a result, the remote expert may be able to suggest the individual(s) and/or team(s) employ specific equipment (e.g., specific surgical implants) during the procedure.

This dynamic delivery platform provides significant benefits. For example, procedures may be enhanced, miscommunications about the individual(s) and/or team(s) performing the procedure are reduced, costs may be decreased, and/or collaboration between individual(s) and/or team(s) and remote experts may be improved.

A detailed discussion of the methods and systems of the invention is provided below. First, a system overview is discussed. Next, the way a user may interact with the system is outlined. Third, the system components are identified. Fourth, a description of a cloud computing system, for the environment of this system, follows. Fifth, the collection and retention of relevant data is disclosed. Finally, additional environments in which this system may be operated is delineated.

System Overview

As disclosed in FIG. 1, the system includes a server comprising a processor aided by memory that communicates with data collection device(s), real-time positioning component(s), and database(s). The data collection devices communicate information related to the subject that will undergo the procedure. The real-time positioning component communicates information related to the location of the individuals who may perform the procedure. The database(s) contains: (1) a plurality of predetermined potential issue manifestations, (2) a plurality of predetermined potential diagnoses, based on the potential issue manifestations, (3) a plurality of predetermined potential procedures for treating the potential diagnoses, and (4) a plurality of available equipment for performing the procedures. Such information may be uploaded to the database by a professional with knowledge of the issue manifestations, diagnoses, procedures, or equipment or an employee, contractor, or agent of the professional. Finally, the processor: (1) actively monitors the location information, (2) determines the availability of the individual based on the location information, (3) notifies the software application of the availability of the individual, (4) actively monitors the subject information, (5) determines a subject diagnosis by comparing the subject information to the issue manifestations, (6) determines a subject procedure by comparing the individual to the potential procedures for treating the subject diagnosis, (7) determines a needed item by comparing the potential equipment to the subject procedure, and (8) notifies the software application of the needed item.

Dynamic Diagnosis of the Subject

All the above referenced information permits the systems and methods to dynamically diagnosis the subject. Indeed, the system takes the information provided by the data collection device(s) and compares the information to the predetermined issue manifestations, which were previously uploaded to the database, to provide a potential diagnosis. The system assigns the diagnosis most closely related to the manifested symptoms detected by the data collection device(s). For example, the data collection device may take and transmit an x-ray of a subject's back to the system. The system may scan the x-ray and identify a hip fracture and provide a subject diagnosis of a hip fracture with specific classification.

The system, however, is not limited to a single diagnosis. Indeed, the system may provide multiple diagnosis, or even update diagnosis as the data collection device(s) provide additional information. For example, the system may originally diagnosis a hip fracture, however, the data collection device(s) may also indicate that the subject is complaining of weakness, lightheadedness, shortness of breath, and other symptoms of shock. Furthermore, the data collection devices may indicate that the subject's blood pressure is dropping. In such a situation the system may not only diagnosis the subject as suffering from a hip fracture but also internal bleeding.

Determination of Appropriate Procedures

The systems and methods next determine appropriate procedures to address the subject diagnosis. The available procedures may be uploaded by an individual who performs the procedure. Conversely, available procedures may be uploaded by third parties with knowledge of the procedures (e.g., members of the American Medical Association, healthcare providers, professionals at the FDA or insurance companies, etc.). Such updated information may add to or supplant previously stored information. Such information may also be actively uploaded into the system (e.g., an individual actively uploads specific information), or passively uploaded into the system (e.g., the system continuously scans relevant third-party databases for relevant data).

An example of the way procedures may be dynamically added or remove may include the treatment of ovarian cancer. In 2014 the FDA issued a warning against the use of laparoscopic power morcellation in most women undergoing myomectomy and hysterectomy for the treatment of fibroids, citing the risk of dissemination of an occult malignancy. As a result, if the subject diagnosis was fibroids, the system would not currently recommend the use of laparoscopic power morcellation for myomectomies and hysterectomies. However, if new equipment came on the market that resulted in the FDA issuing a notification revoking the warning provided the surgical team used the new equipment, the system may then recommend the use of laparoscopic power morcellation for myomectomies and hysterectomies.

In another embodiment, the system may initially determine that more than one procedure may be appropriate to address the subject diagnosis and then use information related to the individual(s) and/or team(s) performing the procedure to narrow down the list of appropriate procedures. For example, based on the information from the data collection devices the system may determine that the subject's knee is not responding to medication(s) and/or treatment(s). As a result, the system may diagnosis the subject's knee as needing to be totally replaced (i.e., a total knee replacement ("TKR")). However, the system may determine that TKR procedures that both remove and preserve the posterior cruciate ligament are appropriate. In such an embodiment, the system may further refine the identification of the appropriateness of the procedure based on the individual(s) and/or team(s) and equipment available to perform the procedures. For example, if an individual that has never removed the posterior cruciate ligament in a TKR the system will select a TKR based on the preservation of the posterior cruciate ligament.

Finally, in a non-limiting embodiment, the system may determine that more than one procedure may be required. In such a case, the system may or may not dynamically rank the procedures. In such an embodiment, the system may identify the equipment used for each procedure separately or together.

Identification of Individuals to Perform the Procedures

The systems and methods employ real-time positioning components to identify individual(s) capable of performing the procedures. Examples of real time positioning system components are GPS, Wi-Fi enabled real time tracking, Bluetooth, and Near Field Communication. Such systems can provide the location data necessary to monitor the real-time position of the individual. When a procedure is identified, the real time positioning system component determines the individual's location at set intervals or continuously, and the device transmits the individual's location data to the server. Specifically, the processor determines the individual's estimated time of arrival ("ETA") at the site at which the procedure will be performed based on the individual's location data.

In one embodiment, to determine the individual's ETA, the system first determines the distance between the individual and the site at which the procedure will be performed from the real-time positioning device. Using information from the real-time positioning device, the system determines how fast the individual is approaching the site. From these two pieces of information, the system determines the individual's ETA at the site. Additional information, such as traffic conditions described below, may be incorporated into the ETA calculation. In some embodiments of the invention the ETA is updated at a set interval. The set interval can be continuous and result in real time updates to the individual's ETA. In this manner, the system can dynamically identify and determine the availability of individual(s) capable of performing the procedure.

By way of example, if the system identifies two individuals who are both in the hospital and capable of performing the identified procedure, but the location information for one of the individuals alerts the system that individual is in an operating room, the system automatically selects the other individual. Similarly, if one individual is located at the hospital, but an individual with more experience performing the identified procedure is 10 miles away at home, the system may first determine the ETA of the more experience individual and, if the procedure is not time sensitive (e.g., the procedure is a scheduled outpatient procedure), the system may assign the more experienced individual. Conversely, if the procedure is time sensitive (e.g., the procedure is the result of a serious car accident), the system may consider the time it will take the more experienced individual to travel to the site and potentially assign the individual already on site to perform the procedure.

Identification of Equipment for Subject Procedure

With the subject diagnosed, procedure chosen and the individuals to perform the procedure identified, the system next identifies the equipment to assist the individual(s) in performing the procedure. In one embodiment, the identified equipment is tailored to the individual(s) identified. For example, a right-handed surgeon may perform the same procedure in a different manner from a left handed surgeon, thereby requiring different equipment.

System Interaction with Users

Although the disclosed system may proceed automatically, individual(s) and/or team(s) may interact with users. For example, in one embodiment a user may audit or change the system's selections. This section describes a non-limiting, exemplary embodiments of such interactions in which a professional may review, approve, or change any aspect of the procedure or equipment identified by the system.

User Login

The first step of the software application is for the user to login. In one embodiment, the system provides for multi-role support. For example, the user may be a healthcare administrator, a nurse/doctor/surgeon, someone in the hospital's center for personalized diagnostics ("CPD"), or an insurance professional.

Figure 3:
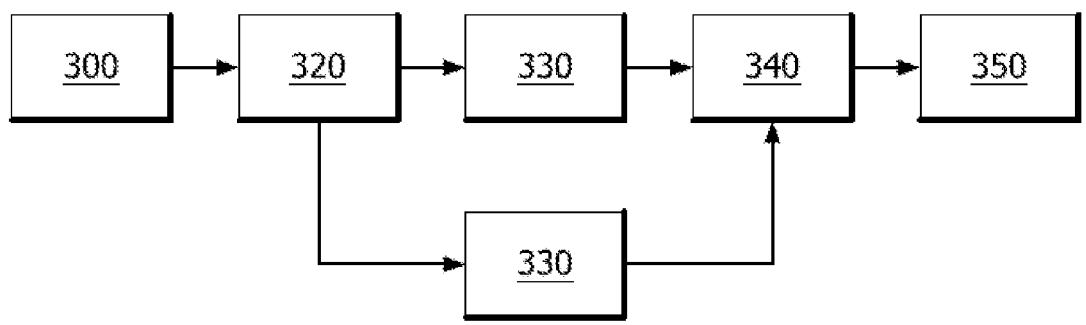
FIG. 3 shows a flow chart of one embodiment of the user login module.

FIG. 3 depicts one embodiment of the login process. The user begins by visiting a website or loading a computer application 300. A server determines if this is the first visit by the user 310. If the server determines this is a subsequent visit, prior general information (e.g., name, contact information, payment method, etc.) is loaded 320. If this is the first visit by the user, the same general information is collected 330. Once the user is identified, they are permitted to sign into the application 340. Upon signing in, the user arrives at the landing page 350. In one non-limiting embodiment, the landing page is dynamic and may display different information depending on the role of the user (i.e., an insurance professional would be presented with the different landing page than a surgeon, who would themselves see a different page from a hospital administrator).

Equipment Selection

In one embodiment, the ability to review or change the equipment or procedure depends on the role of the user. For example, if the user signs in as a nurse, the system may restrict the user to only viewing a list of equipment to perform the procedure. Conversely, a surgeon may be permitted to not only change the equipment but also the procedure. Furthermore, certain users may be permitted to swap out only certain pieces of equipment.

Figure 4:
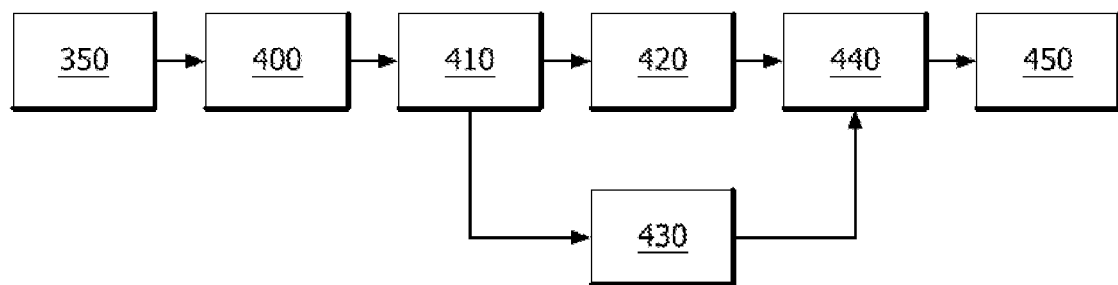
FIG. 4 shows a flow chart of one embodiment of module where an authorized user may change the equipment selected by the system.

Such an equipment restriction is depicted in FIG. 4 wherein a healthcare provider is the only user that may swap out the implant selected by the system (i.e., an insurance professional would be restricted from accessing such options). Indeed, after signing in 350, the healthcare provider retrieves the patient's information 400. The healthcare provider may then review information from the relevant data collection devices (e.g., x-rays) 410. The healthcare provider may then pull up and review the selected procedure 420. The healthcare provider may even change the selected procedure 430. Furthermore, the healthcare provider, much like the system, may even identify multiple procedures for which equipment should be gathered 430. After the procedures are reviewed or selected, the healthcare provider may review the list of equipment 440. Finally, the healthcare professional may even request or schedule a consult with a remote professional 450.

Figure 5:
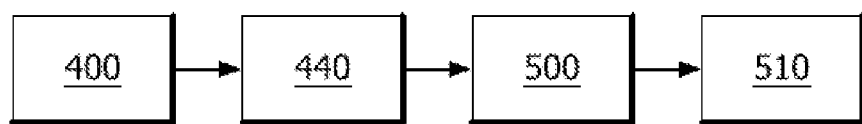
FIG. 5 shows a flow chart of one embodiment of an equipment selection audit module.

In another embodiment, the system may further include an option to audit the equipment selected for the procedure. FIG. 5 depicts one embodiment of such an equipment selection audit. In such an embodiment, a professional may first view the patient's case 400 and a list of the required equipment with which to stock the operating case cart 440. Indeed, the professional may even view the preferences of the individuals that will be performing the procedure 500. In a further embodiment, the system may highlight the equipment preferred by the individual or place such equipment at the top of any list of available equipment which may ease of the performance of the audit 510.

Equipment Coordination

Figure 6:
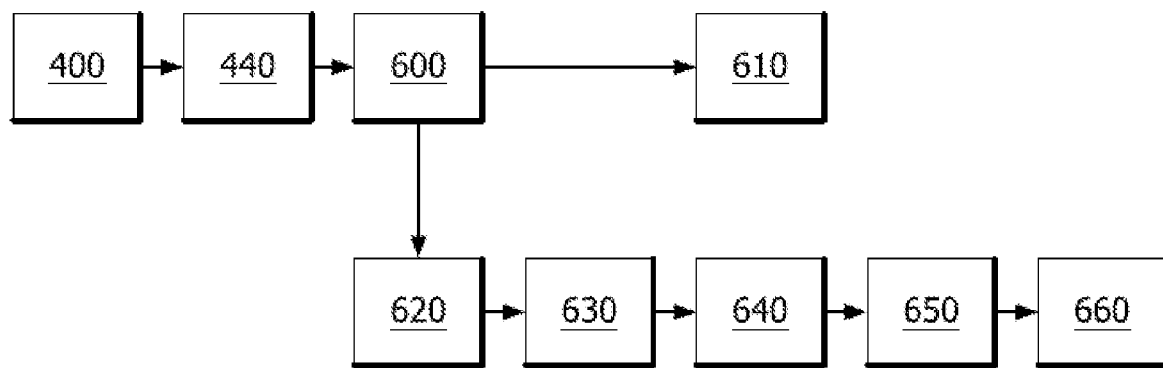
FIG. 6 shows a flow chart of one embodiment of an equipment assembly module.

Once the desired equipment has been identified, the system may coordinate its assembly. In one embodiment in the healthcare space, the assembly of the equipment will take the form of the stocking of an operating room case cart, which may also be referred to as a cart build. FIG. 6 depicts one embodiment of the steps of such a cart build. In the cart build module, a hospital employee may review a patient's case 400 and a list of equipment selected to perform a procedure 440. The employee may then proceed to place all the identified equipment on the surgical cart 600. If the cart is completed, an alert may be sent to the individual(s) and/or team performing the procedure 610. Conversely, if a piece of equipment is unavailable, the system may automatically suggest a substitute piece of equipment, identify how the missing piece of equipment may be constructed from available equipment, or place a hold on the case 620. The system may automatically alert the individual(s) and/or team(s) performing the procedure if the system suggests a substitute piece of equipment or identifies how the missing piece of equipment may be constructed from available equipment 630. Such an alert may allow the individual(s) and/or team(s) to approve or reject the suggested substitute piece of equipment 640. If the cart is unable to be built, a hold may be placed on the case 650. If a hold is placed on the case 650, the system may send a notice of such a hold to the healthcare provider and/or the individual(s) and/or team scheduled to perform the procedure 660.

Figure 7:
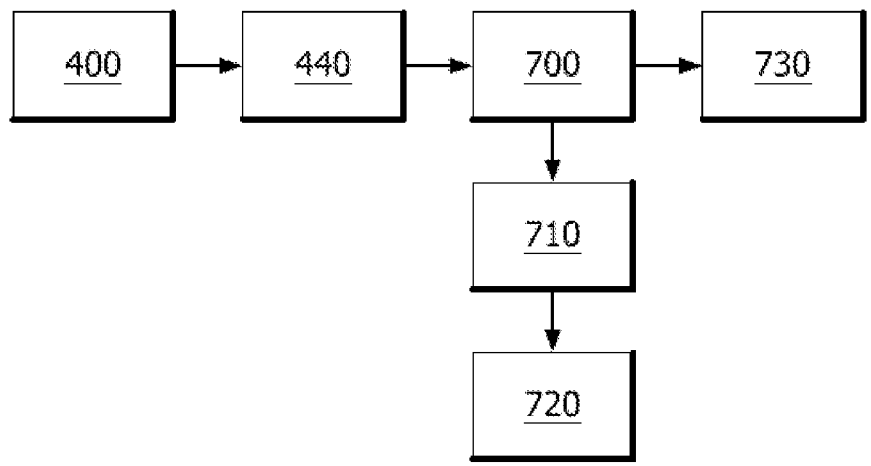
FIG. 7 shows a flow chart of one embodiment of an equipment assembly audit module.

In another embodiment, the equipment list placed on the cart may be audited by a healthcare professional. FIG. 7 depicts the steps of one embodiment of such a cart audit. In such an audit, a healthcare professional (e.g., a circulating nurse) reviews a patient's case 400 and the cart build 440. Next the professional reviews the contents of the cart to confirm all equipment identified by the system is contained in the cart 700. If an item is missing from the cart, then the professional has the option to place the case on hold 710. If a hold is placed on the case, the system may send a notice of such a hold to the healthcare provider and/or the individual(s) and/or team scheduled to perform the procedure 720. If the healthcare professional approves the cart build, then the system may send a notice of such approval to the healthcare provider and/or the individual(s) and/or team scheduled to perform the procedure 730.

Procedure Monitoring

Figure 8:
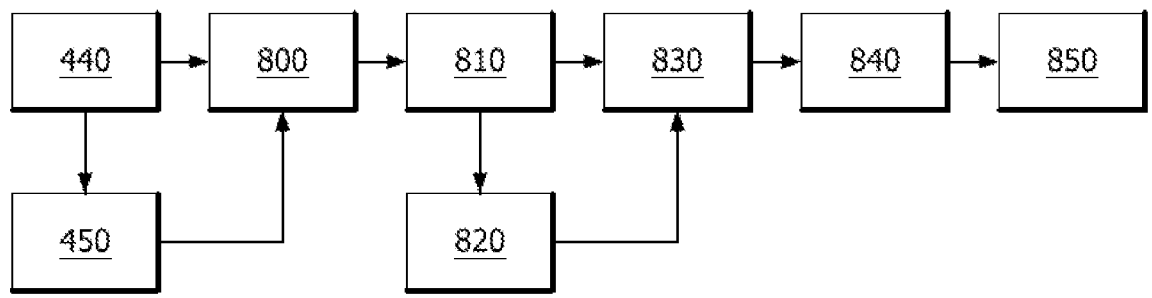
FIG. 8 shows a flow chart of one embodiment of a procedural monitoring module.

In a non-limiting embodiment, the system may monitor the progress of the procedure. FIG. 8 depicts the steps of one embodiment of such monitoring. First, the system may permit an individual to review what equipment has been gathered for the procedure 440. Second, the individual may elect to request a consultation with a remote professional 450. Third, the availability of the site at which the procedure is to be performed is confirmed 800. Fourth, the presence of the individual(s) and/or team(s) performing the procedure at the site is confirmed 810. If the individual(s) and/or team(s) performing the procedure are not at the site, then the system may send a notification alerting them to proceed to the site 820. Fifth, the steps of the procedure are displayed 830. The system may further note when each step is satisfied, and/or the equipment utilized in performing each step. Furthermore, if an issue arises during a step in the procedure, the system may identify whether the issue is known. Such identification may be based on data previously uploaded by healthcare professionals or retained by the system. If the issue is known, the system may provide recommendations as to how such issues were previously overcome. Conversely, if the issue is new, the system may provide the individual(s) and/or team(s) performing the procedure the options to bring in a remote expert 450. Sixth, after the last step of the procedure, the system may identify what equipment should be present on the cart 840. Such a notification may prevent a piece of equipment from being lost during the procedure. Seventh, the system may request all individual(s) and/or team(s) performing the procedure acknowledge they assisted in performing the procedure 850. Once completed, the system may close the case.

System Components

A non-limiting embodiment of the system includes a general-purpose computing device, including a processing unit (CPU or processor), and a system bus that couples various system components including the system memory such as read only memory (ROM) and random-access memory (RAM) to the processor. The system can include a storage device connected to the processor by the system bus. The system can include interfaces connected to the processor by the system bus. The system can include a cache of high-speed memory connected directly with, in close proximity to, or integrated as part of the processor. The system can copy data from the memory and/or a storage device to the cache for quick access by the processor. In this way, the cache provides a performance boost that avoids processor delays while waiting for data. These and other modules stored in the memory, storage device or cache can control or be configured to control the processor to perform various actions. Other system memory may be available for use as well. The memory can include multiple different types of memory with different performance characteristics.

Computer Processor

The invention may operate on a computing device with more than one processor or on a group or cluster of computing devices networked together to provide greater processing capability. The processor can include any general-purpose processor and a hardware module or software module, stored in an external or internal storage device, configured to control the processor as well as a special-purpose processor where software instructions are incorporated into the actual processor design. The processor may essentially be a completely self-contained computing system, containing multiple cores or processors, a bus, memory controller, cache, etc. A multi-core processor may be symmetric or asymmetric.

For clarity purposes, an illustrative system embodiment is presented as including individual functional blocks including functional blocks labeled as a "processor". The functions such blocks represent may be provided through the use of either shared or dedicated hardware, including, but not limited to, hardware capable of executing software and hardware, such as a processor, that is purpose-built to operate as an equivalent to software executing on a general-purpose processor. For example, the functions of one or more processors may be provided by a single shared processor or multiple processors and use of the term "processor" should not be construed to refer exclusively to hardware capable of executing software. Illustrative embodiments may include microprocessor and/or digital signal processor (DSP) hardware, read-only memory (ROM) for storing software performing the operations discussed below, and random-access memory (RAM) for storing results. Very large-scale integration (VLSI) hardware embodiments, as well as custom VLSI circuitry in combination with a general purpose DSP circuit, may also be provided.

System Bus

The system bus may be any of several types of bus structures including a memory bus or memory controller, a peripheral bus, and a local bus using any of a variety of bus architectures. A basic input/output (BIOS) stored in ROM or the like, may provide the basic routine that helps to transfer information between elements within the computing device, such as during start-up.

Storage Device

The computing device can further include a storage device such as a hard disk drive, a magnetic disk drive, an optical disk drive, a solid-state drive, a tape drive or the like. Like the system memory, a storage device may be used to store data files, such as location information, menus, software, wired and wireless connection information (e.g., information that may enable the mobile device to establish a wired or wireless connection, such as a USB, Bluetooth or wireless network connection), and any other suitable data. Specifically, the storage device and/or the system memory may store code and/or data for carrying out the disclosed techniques among other data.

In one aspect, a hardware module that performs a function includes the software component stored in a non-transitory computer-readable medium in connection with the necessary hardware components, such as the processor, bus, display, and so forth, to carry out the function. The basic components are known to those of skill in the art and appropriate variations are contemplated depending on the type of device, such as whether the device is a small, handheld computing device, a desktop computer, or a computer server.

Although an embodiment described herein employs cloud computing and cloud storage, it should be appreciated by those skilled in the art that other types of computer readable media which can store data that are accessible by a computer, such as magnetic cassettes, flash memory cards, digital versatile disks, cartridges, random access memories (RAMS), read only memory (ROM), a cable or wireless signal containing a bit stream and the like, may also be used in the operating environment. Furthermore, non-transitory computer-readable storage media as used herein include all computer-readable media, with the sole exception being a transitory propagating signal per se.

Interface

To enable user interaction with the computing device, an input device represents any number of input mechanisms, such as a microphone for speech, a web camera for video, a touch-sensitive screen for gesture or graphical input, keyboard, mouse, motion input, speech and so forth. An output device can also be one or more of several output mechanisms known to those of skill in the art such as a display screen, speaker, alarm, and so forth. In some instances, multimodal systems enable a user to provide multiple types of input to communicate with the computing device. The communications interface generally governs and manages the user input and system output. Furthermore, one interface, such as a touch screen, may act as an input, output and/or communication interface.

There is no restriction on operating on any hardware arrangement and therefore the basic features here may easily be substituted for improved hardware or firmware arrangements as they are developed.

Data Collection Devices

The system includes at least one data collection device for monitoring the subject. The data collection device may take many forms. For example, the data collection device may be an auditory data collection device (e.g., microphone), an image data collection device (e.g., camera), a biometric data collection device (e.g., pulse detector or blood pressure monitor), a motion detector, a proximity sensor, or a combination thereof (e.g., a camera which is configured to also measure the pulse of the subject). The data collection device may also monitor less obvious behaviors, such as a subject's response to touch and/or temperature.

In one non-limiting embodiment, the data collection device may be mounted on a wearable device, such as a headset or glasses. The wearable device may, again, include biometric data collection devices, such as a pulse detection sensor, pupil dilation sensors, a three-axis accelerometer, a GPS module, an RF data collection device, an RFID or NFC chip, a galvanic skin response sensor, or other data collection device to detect stress or proximity to procedure site. Such a wearable data collection device may be configured to alarm or vibrate if the data collection device detects additional symptom manifestations which may require immediate intervention prior to the procedure.

In one embodiment, the data collection device includes electronic components for wired or wireless communication with the system. As a result, the data collection device may avoid interference with the procedure. In one embodiment, the data collection device is replaceable or added to, such that different data collection devices may be removed, which may allow the data collection device to be cleaned.

In another embodiment, the data collection device may include an embedded monitoring component that is configured to verify the identity of the user and monitor the procedure. For example, the data collection device may employ facial recognition software or finger print analysis to confirm the identity of the subject at set intervals or continuously.

The system may include more than one data collection device. Indeed, the system may include 2, 3, 4, 5, 6, 7, 8, 9, or 10 data collection devices. For example, the system may include a camera, a microphone, and three biometric data collection devices.

In one embodiment, the data collection devices may be contained within a tamper-proof housing to prevent the subject from removing the data collection device.

Real-Time Positioning Component

The real-time positioning system component can be a global positioning system (GPS) component used to identify the current geographic location of the individual and/or computer system as well as its location in relation to another location (e.g., the site at which the procedure is to be performed). GPS information can be displayed on the system. For example, a map may be displayed on the mobile device and as outlined below directions to the site at which the procedure is to be performed may be provided to the individual who is to perform the procedure. The GPS information may be supplemented by other information, such as nearby wireless networks, to determine the current location of the mobile device. For example, in certain embodiments, the mobile device may identify its current location by sensing and/or identifying nearby Wi-Fi networks. The mobile device may be able to identify the geographic location of such Wi-Fi networks and thus, identify its own location based on which Wi-Fi networks it detects and its proximity to the Wi-Fi networks (i.e., Wi-Fi enabled real time tracking).

In one embodiment, the system may use the real time positioning component to determine if an individual is available to perform the procedure. For example, if the system determines that an individual is currently located at the site of another procedure (e.g., in another operating room), the system may remove that occupied individual from consideration for the current procedure. If such a situation arises, the system may proceed to identify other individuals capable of performing the procedure desired. The system may even dynamically identify alternate procedures based on individuals' availability.

Software Operations

The logical operations of the various embodiments disclosed are implemented as: (1) a sequence of computer implemented steps, operations, or procedures running on a programmable circuit within a general use computer, (2) a sequence of computer implemented steps, operations, or procedures running on a specific-use programmable circuit; and/or (3) interconnected machine modules or program engines within the programmable circuits. The system can practice all or part of the recited methods, can be a part of the recited systems, and/or can operate according to instructions in the recited non-transitory computer-readable storage media. Such logical operations can be implemented as modules configured to control the processor to perform functions according to the programming of the module. For example, if a storage device contains modules configured to control the processor, then these modules may be loaded into RAM or memory at runtime or may be stored as would be known in the art in other computer-readable memory locations. Having disclosed some components of a computing system, the disclosure now turns to a description of cloud computing, which is the preferred environment of the invention.

Cloud System

Cloud computing is a type of Internet-based computing in which a variety of resources are hosted and/or controlled by an entity and made available by the entity to authorized users via the Internet. A cloud computing system can be configured, wherein a variety of electronic devices can communicate via a network for purposes of exchanging content and other data. The system can be configured for use on a wide variety of network configurations that facilitate the intercommunication of electronic devices. For example, each of the components of a cloud computing system can be implemented in a localized or distributed fashion in a network.

Cloud Resources

The cloud computing system can be configured to include cloud computing resources (i.e., "the cloud"). The cloud resources can include a variety of hardware and/or software resources, such as cloud servers, cloud databases, cloud storage, cloud networks, cloud applications, cloud platforms, and/or any other cloud-based resources. In some cases, the cloud resources are distributed. For example, cloud storage can include multiple storage devices. In some cases, cloud resources can be distributed across multiple cloud computing systems and/or individual network enabled computing devices. For example, cloud computing resources can communicate with a server, a database, and/or any other network enabled computing device to provide the cloud resources.

In some cases, the cloud resources can be redundant. For example, if cloud computing resources are configured to provide data backup services, multiple copies of the data can be stored such that the data is still available to the user even if a storage resource is offline, busy, or otherwise unavailable to process a request. In another example, if a cloud computing resource is configured to provide software, then the software can be available from different cloud servers so that the software can be served from any of the different cloud servers. Algorithms can be applied such that the closest server or the server with the lowest current load is selected to process a given request.

User Terminal

A user interacts with cloud computing resources through user terminals or testing devices connected to a network by direct and/or indirect communication. Cloud computing resources can support connections from a variety of different electronic devices, such as servers; desktop computers; mobile computers; handheld communications devices (e.g., mobile phones, smart phones, tablets); set top boxes; network-enabled hard drives; and/or any other network-enabled computing devices. Furthermore, cloud computing resources can concurrently accept connections from and interact with multiple electronic devices. Interaction with the multiple electronic devices can be prioritized or occur simultaneously.

Cloud computing resources can provide cloud resources through a variety of deployment models, such as public, private, community, hybrid, and/or any other cloud deployment model. In some cases, cloud computing resources can support multiple deployment models. For example, cloud computing resources can provide one set of resources through a public deployment model and another set of resources through a private deployment model.

In some configurations, a user terminal can access cloud computing resources from any location where an Internet connection is available. However, in other cases, cloud computing resources can be configured to restrict access to certain resources such that a resource can only be accessed from certain locations. For example, if a cloud computing resource is configured to provide a resource using a private deployment model, then a cloud computing resource can restrict access to the resource, such as by requiring that a user terminal access the resource from behind a firewall.

Service Models

Cloud computing resources can provide cloud resources to user terminals through a variety of service models, such as Software as a Service (SaaS), Platforms as a service (PaaS), Infrastructure as a Service (IaaS), and/or any other cloud service models. In some cases, cloud computing resources can provide multiple service models to a user terminal. For example, cloud computing resources can provide both SaaS and IaaS to a user terminal. In some cases, cloud computing resources can provide different service models to different user terminals. For example, cloud computing resources can provide SaaS to one user terminal and PaaS to another user terminal.

User Interaction

In some cases, cloud computing resources can maintain an account database. The account database can store profile information for registered users. The profile information can include resource access rights, such as software the user is permitted to use, maximum storage space, etc. The profile information can also include usage information, such as computing resources consumed, data storage location, security settings, personal configuration settings, etc. In some cases, the account database can reside on a database or server remote to cloud computing resources such as servers or database.

Cloud computing resources can provide a variety of functionality that requires user interaction. Accordingly, a user interface (UI) can be provided for communicating with cloud computing resources and/or performing tasks associated with the cloud resources. The UI can be accessed via an end user terminal in communication with cloud computing resources. The UI can be configured to operate in a variety of client modes, including a fat client mode, a thin client mode, or a hybrid client mode, depending on the storage and processing capabilities of cloud computing resources and/or the user terminal. Therefore, a UI can be implemented as a standalone application operating at the user terminal in some embodiments. In other embodiments, a web browser-based portal can be used to provide the UI. Any other configuration to access cloud computing resources can also be used in the various embodiments.

Collection of Data

In some configurations, during the diagnosis and/or procedures described above, a storage device or resource can be used to store relevant data transmitted from the data collection device(s). Such information may be used by the system to further refine diagnoses in the future. In such an embodiment, the system may engage in machine learning. Such learning will permit more efficient subject diagnosis in the future.

In one embodiment, the data collection devices may provide information related to the subject's height, weight, age, race, gender, and/or prior procedures procedure(s). After the procedure is complete, the individual(s) performing the procedure may update the database with additional information related to the specific subject. As a result, the system may be able to determine that individuals who had previously received a cardiovascular stent suffered specific complications during the procedure and to overcome such complications additional equipment or consultations with remote experts were required. In the future, the system may include such equipment or contact such experts prior to the procedure. In this way, the data may be used to dynamically adjust the recommended equipment, procedure(s), individual(s) and/or team(s) who are to perform the procedure, and/or automatically contact remote experts for consultation purposes.

In another embodiment, the data collection device(s) may capture specific tendencies of the individual(s) and/or team(s) performing the procedure. The system may utilize such information to immediately or in the future suggests adjustments to the recommended procedure and/or needed equipment. Indeed, the system may be a dynamic system that through use learns the preferences and tendencies of the individual(s) and/or team(s) performing the procedure. By learning such preferences and/or tendencies the system may increase the efficiencies and/or lower the cost of the procedures.

The data stored may also be incorporated into the disclosed system and methods to refine the procedure or evaluate efficacy of the procedure. For example, if a subject population experiences an increase in negative outcomes from one specific procedure, the system may notify individual(s) and/or team(s) performing the procedure of such a potential pattern. Such a notification may increase the preparedness of the individual and/or team to react to any manifestations of such negative outcomes. Furthermore, the information collected may serve more than one purpose (measurements of positive outcomes, dynamic avoidance of negative outcomes, learning individual(s) and/or team preferences, and others). Those purposes may also be routinely evaluated and/or updated.

The system also contemplates that this gathered data might include personal and/or sensitive data in some instances. The system further contemplates that the entities responsible for the collection, analysis, disclosure, transfer, storage, or other use of such data should implement and consistently use privacy policies and practices that are generally recognized as meeting or exceeding industry or governmental requirements for maintaining personal information data private and secure. For example, personal data from subjects should be collected for legitimate and reasonable uses of the entity and not shared or sold outside of those legitimate uses. Further, such collection should occur only after the informed consent of the subjects. Additionally, such entities should take any needed steps for safeguarding and securing access to such personal data and ensuring that others with access to the personal data adhere to their privacy and security policies and procedures. Further, such entities can subject themselves to evaluation by third parties to certify their adherence to widely accepted privacy policies and practices.

Additional Environments

The systems and methods provide for dynamic management of procedures. In one embodiment, the procedures are healthcare related, such as surgical procedure. However, the system is not restricted solely to surgical procedures. Indeed, the system may be used to dynamically manage any type of procedures. For example, the system may dynamically manage automobile or structural repair. As a result, although the system is discussed above primarily in relation to healthcare application, the system is not restricted solely to healthcare applications.

Automotive Repair

In one embodiment, the environment in which the disclosed system and method operates is automobile repair. In such a configuration, the subject is not a human patient, but is instead an automobile. The individuals performing the procedure are not a surgical team but are instead mechanics. Furthermore, the procedures are not surgical procedures, but instead, automobile repairs.

In such an environment, mechanics, and possibly other automobile and parts professional, may upload the necessary information to the database (e.g., issue manifestations, potential diagnoses, repair procedures, or available equipment for performing the repairs).

Structural Repair

In one embodiment, the environment in which the disclosed system and method operates is structural repairs. In such a configuration, the subject is not a human patient, but is instead a structure. The individuals performing the procedure are not a surgical team but are instead contractors. Furthermore, the procedures are not surgical procedures, but instead, structural repairs.

In such an environment, contractors, and possibly other construction or insurance professionals, may upload the necessary information to the database (e.g., issue manifestations, potential diagnoses, repair procedures, or available equipment for performing the repairs).

While this subject matter has been disclosed with reference to specific embodiments, it is apparent that other embodiments and variations can be devised by others skilled in the art without departing from the true spirit and scope of the subject matter described herein. The appended claims include all such embodiments and equivalent variations.

What is claimed is:

1. A system for dynamically diagnosing a subject and coordinating personnel and equipment for enhanced performance of a procedure, the system comprising:
   a software application, the application operating on a mobile computer device or on a computer device, which is in communication with at least one data collection device for monitoring the subject and at least one positioning system component linked to an individual who has previously performed the procedure, the application is configured to receive subject information from the data collection device and location information from the individual, and to communicate the subject information and location information through a wired and/or wireless communication network to a server located at a site where the procedure is to be performed or at a location remote from the site; and
   a processor that is in communication through the wired and/or wireless communication network with the software application, as well as the server, the processer is configured to call up from a database of the system, upon communication of the subject information and location information to the server:
      a plurality of predetermined potential issue manifestations,
      a plurality of predetermined potential diagnoses, based on the potential issue manifestations,
      a plurality of predetermined potential procedures for treating the potential diagnoses, and
      a plurality of available equipment for performing the procedures;
      wherein the issue manifestations, diagnoses, procedures, and equipment have been previously uploaded to the database by a professional with knowledge of the issue manifestations, diagnoses, procedures, or equipment or an employee, contractor, or agent of the professional;
   whereby the processor is configured to:
      monitor the location information,
      determine the availability of the individual based on the location information,
      notify the software application of the availability of the individual,
      monitor the subject information,
      determine a subject diagnosis by comparing the subject information to the issue manifestations,
      determine a subject procedure by comparing the individual to the potential procedures for treating the subject diagnosis,
      determine a needed item by comparing the potential equipment to the subject procedure, and
      notify the software application of the needed item.

2. The system of claim 1 wherein the data collection device is selected from the group consisting of: an auditory device, an image capture device, a biometric device, a motion detector, a proximity sensor, or a combination thereof.

3. The system of claim 1 wherein the data collection device is a wearable device.

4. The system of claim 1 further comprising a second positioning component attached to the equipment to perform the procedure.

5. The system of claim 4 wherein the processor is further configured to monitor the location of the equipment using the second positioning component.

6. The system of claim 4 wherein the processor is further configured to determine an estimated time of arrival at the site of both: (a) the individual at the site based on the positioning component and (b) the equipment based on the second positioning component.

7. The system of claim 6 wherein the processor is further configured to notify the individual of the estimated time of arrival of the equipment at the site.

8. The system of claim 1 wherein the processor is configured to permit a professional, who is at a location remote from the site, to interact with the individual.

9. The system of claim 8 wherein the interaction occurs via a laser pointer located at the site.

10. A method for dynamically diagnosing a subject and coordinating personnel and equipment for enhanced performance of a procedure, the method comprising:
receiving information pertaining to: (1) the subject from a data collection device and (2) an individual who has previously performed the procedure from a positioning system component with a server or a remote server using a software application operating on a mobile computer device or a computer device that may be synced with the mobile computer device, and wherein the mobile computer device or the computer device communicate through a wired and/or wireless communication network with the server at a site the procedure will be performed or with the remote server in a location that is remote to the site and in communication with the server;
upon receiving the information, calling up from a database using a processor: (1) a plurality of predetermined potential issue manifestations, (2) a plurality of predetermined potential diagnoses, based on the potential issue manifestations, (3) a plurality of predetermined potential procedures for treating the potential diagnoses, and (4) a plurality of available equipment for performing the procedures; wherein the issue manifestations, diagnoses, procedures, and equipment have been previously uploaded to the database by a professional with knowledge of the issue manifestations, diagnoses, procedures, or equipment or an employee, contractor, or agent of the professional;
tracking a location of the individual and determining the availability of the individual to perform the procedure based on the location information;
notifying the software application of the availability of the individual;
monitoring the data collection device information and determining a subject diagnosis by comparing the data collection device information with the issue manifestations;
determining a subject procedure by comparing the individual to the potential procedures for treating the subject diagnosis;
determining a needed item by comparing the potential equipment to the subject procedure; and
notifying the software application of the needed item.

11. The method of claim 10 wherein the data collection device is selected from the group consisting of: an auditory device, an image capture device, a biometric device, a motion detector, a proximity sensor, or a combination thereof.

12. The method of claim 10 wherein the data collection device is mounted on a wearable device.

13. The method of claim 10 further comprising receiving information pertaining to a second positioning component attached to the equipment to perform the procedure.

14. The method of claim 13 wherein the processor monitors the location of the equipment using the second positioning component.

15. The method of claim 13 further comprising:
determining an estimated time of arrival at the site of both: (a) the individual at the site based on the positioning component and (b) the equipment based on the second positioning component; and
notifying the individual of the estimated time of arrival of the equipment at the site.

16. The system of claim 10 further comprising a professional, who is at a location remote from the site, interacting with the individual.

17. The system of claim 16 wherein the interacting occurs via a laser pointer located at the site.

* * * * *